United States Patent [19]

Fink

[11] Patent Number: 5,508,266

[45] Date of Patent: Apr. 16, 1996

[54] GEM-DISUBSTITUTED AMINO ACID DERIVATIVES

[75] Inventor: Cynthia A. Fink, Lebanon, N.J.

[73] Assignee: Ciba-Geigy Corporation, Tarrytown, N.Y.

[21] Appl. No.: 263,855

[22] Filed: Jun. 22, 1994

[51] Int. Cl.⁶ .................... A61K 38/05; C07C 327/06; C07C 323/41

[52] U.S. Cl. .................. 514/19; 548/495; 549/76; 558/254; 560/16; 562/426

[58] Field of Search ................ 558/254; 560/16; 562/426; 514/513, 542, 562, 19

[56] References Cited

U.S. PATENT DOCUMENTS

| | | | |
|---|---|---|---|
| 4,613,587 | 9/1986 | Kessler et al. | 514/19 |
| 4,684,660 | 8/1987 | Ondetti et al. | 514/423 |

FOREIGN PATENT DOCUMENTS

| | | |
|---|---|---|
| 0524553 | 1/1993 | European Pat. Off. . |
| 2207351 | 2/1989 | United Kingdom . |

OTHER PUBLICATIONS

Yukio, S. et al. *Chem. Abstr.* 1979, 90(15), 116647; *Bioinorg Chem.* 1978, 9(6), 521–528.

Holden, H. M. et al. *J. Biol. Chem.* 1988, 263(7), 3256–3260.

Kortylewicz, Z. P. et al. *J. Med. Chem.* 1990, 33, 263–273.

*Primary Examiner*—Johann Richter
*Assistant Examiner*—Michael G. Ambrose
*Attorney, Agent, or Firm*—Norbert Gruenfeld

[57] ABSTRACT

Disclosed are the compounds of formula I

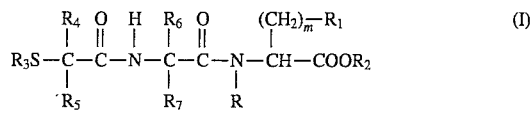

wherein

R represents hydrogen, lower alkyl, carbocyclic or heterocyclic aryl-lower alkyl or cycloalkyl-lower alkyl;

$R_1$ represents hydrogen, lower alkyl, cycloalkyl, carbocyclic aryl or heterocyclic aryl, or biaryl;

$R_3$ represents hydrogen or acyl;

$R_4$ represents hydrogen, lower alkyl, carbocyclic or heterocyclic aryl, carbocyclic or heterocyclic aryl-lower alkyl, cycloalkyl, cycloalkyl-lower alkyl, biaryl or biaryl-lower alkyl;

$R_5$ represents hydrogen or lower alkyl; or $R_4$ and $R_5$ together with the carbon atom to which they are attached represent cycloalylidene or benzo-fused cycloalkylidene;

$R_6$ represents lower alkyl, carbocyclic or heterocyclic aryl, carbocyclic or heterocyclic aryl-lower alkyl, cycloalkyl, cycloalkyl-lower alkyl, biaryl or biaryl-lower alkyl;

$R_7$ represents lower alkyl, carbocyclic or heterocyclic aryl-lower alkyl, cycloalkyl-lower alkyl or biaryl-lower alkyl;

m is 0, 1, 2 or 3; and $COOR_2$ represents carboxyl or carboxyl derivatized in form of a pharmaceutically acceptable ester; disulfide derivatives derived from said compounds wherein $R_3$ is hydrogen; and pharmaceutically acceptable salts thereof; pharmaceutical compositions comprising said compounds; methods for preparation of said compounds; intermediates; and methods of treating disorders in mammals which are responsive to ACE and NEP inhibition by administration of said compounds to mammals in need of such treatment.

6 Claims, No Drawings

GEM-DISUBSTITUTED AMINO ACID DERIVATIVES

SUMMARY OF THE INVENTION

The present invention is directed to novel gem-disubstituted amino acid derivatives described below which are useful as angiotensin converting enzyme (ACE) inhibitors and as neutral endopeptidase (NEP, EC 3.4.24.11) inhibitors. The compounds of the invention are particularly useful for the treatment of conditions which are responsive to ACE and NEP inhibition, particularly cardiovascular disorders, such as hypertension, renal insufficiency (including edema and salt reduction), pulmonary edema, congestive heart failure and atherosclerosis. The compounds of the invention are also useful for reducing elevated cholesterol plasma levels in mammals.

By virtue of their inhibition of neutral endopeptidase, the compounds of the invention may also be useful for the treatment of pain, depression, certain psychotic conditions, and cognitive disorders. Other potential indications include the treatment of angina, premenstrual syndrome, Meniere's disease, hyperaldosteronism, hypercalciuria, ascites, glaucoma, asthma and gastrointestinal disorders such as diarrhea, irritable bowel syndrome and gastric hyperacidity.

DETAILED DESCRIPTION OF THE INVENTION

The present invention relates to cyclic amino acid derivatives of the following formula I

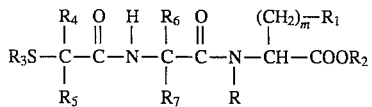

wherein

R represents hydrogen, lower alkyl, carbocyclic or heterocyclic aryl-lower alkyl or cycloalkyl-lower alkyl;

$R_1$ represents hydrogen, lower alkyl, cycloalkyl, carbocyclic aryl or heterocyclic aryl, or biaryl;

$R_3$ represents hydrogen or acyl;

$R_4$ represents hydrogen, lower alkyl, carbocyclic or heterocyclic aryl, carbocyclic or heterocyclic aryl-lower alkyl, cycloalkyl, cycloalkyl-lower alkyl, biaryl or biaryl-lower alkyl;

$R_5$ represents hydrogen or lower alkyl; or $R_4$ and $R_5$ together with the carbon atom to which they are attached represent cycloalylidene or benzo-fused cycloalkylidene;

$R_6$ represents lower alkyl, carbocyclic or heterocyclic aryl, carbocyclic or heterocyclic aryl-lower alkyl, cycloalkyl, cycloalkyl-lower alkyl, biaryl or biaryl-lower alkyl;

$R_7$ represents lower alkyl, carbocyclic or heterocyclic aryl-lower alkyl, cycloalkyl-lower alkyl or biaryl-lower alkyl;

m is 0, 1, 2 or 3; and $COOR_2$ represents carboxyl or carboxyl derivatized in form of a pharmaceutically acceptable ester; disulfide derivatives derived from said compounds wherein $R_3$ is hydrogen; and pharmaceutically acceptable salts thereof.

The present invention is also directed to pharmaceutical compositions comprising said compounds; methods for preparation of said compounds; intermediates; and methods of treating disorders in mammals which are responsive to ACE and NEP inhibition by administration of said compounds to mammals in need of such treatment.

Pharmaceutically acceptable esters are preferably prodrug ester derivatives, such being convertible by solvolysis or under physiological conditions to the free carboxylic acids of formula I.

Encompassed by the instant invention are any prodrug derivatives of compounds of the invention having a free carboxyl, sulfhydryl or hydroxy group, said prodrug derivatives being convertible by solvolysis or under physiological conditions to be the free carboxyl, sulfhydryl and/or hydroxy compounds. Prodrug derivatives are e.g. the esters of free carboxylic acids and S-acyl and O-acyl derivatives of thiols, alcohols or phenols, wherein acyl has meaning as defined herein.

Pharmaceutically acceptable prodrug esters are preferably e.g. lower alkyl esters, aryl-lower alkyl esters, α-(lower alkanoyloxy)-lower alkyl esters such as the pivaloyloxymethyl ester, and α-(lower alkoxycarbonyl- or di-lower alkylamino carbonyl-)-lower alkyl esters.

Pharmaceutically acceptable salts are salts derived from pharmaceutically acceptable bases for any acidic compounds of the invention, e.g. those wherein $COOR_2$ represents carboxyl. Such are e.g. alkali metal salts (e.g. sodium, potassium salts), alkaline earth metal salts (e.g. magnesium, calcium salts), amine salts (e.g. tromethamine salts).

Compounds of formula I, depending on the nature of substituents, possess two or more asymmetric carbon atoms. The resulting diastereomers and optical antipodes are encompassed by the instant invention. The preferred configuration is indicated in formula Ia

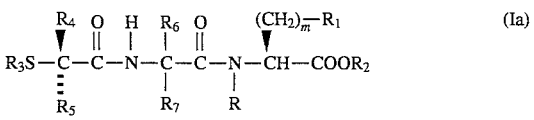

wherein asymmetric carbons with the substituents -$(CH_2)_m R_1$ and -$R_4$ have the S-configuration in general, and wherein R, $R_1$–$R_7$ and m have meaning as defined above.

Preferred are the compounds of formula I and Ia wherein m is one; R and $R_5$ represent hydrogen; $R_1$ represents (monocyclic or bicyclic)-carbocyclic aryl or heterocyclic aryl, or biaryl; $R_3$ represents hydrogen or acyl; $R_4$ represents hydrogen, lower alkyl or carbocyclic or heterocyclic aryl-lower alkyl; $R_5$ represents hydrogen; or $R_4$ and $R_5$ combined with the carbon atom to which they are attached represent $C_5$ or $C_6$ cycloalkylidene; $R_6$ and $R_7$ represent lower alkyl or carbocyclic or heterocyclic aryl-lower alkyl; $COOR_2$ represents carboxyl or carboxyl derivatized in form of a pharmaceutically acceptable ester; disulfide derivatives derived from said compounds wherein $R_3$ is hydrogen; and pharmaceutically acceptable salts thereof.

Further preferred are the compounds of formula II

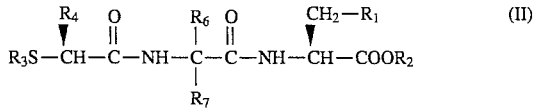

wherein $R_1$ represents lower alkyl, $C_5$- or $C_6$-cycloalkyl, carbocyclic or heterocyclic monocyclic or bicyclic aryl, or biaryl; $R_3$ represents hydrogen or acyl; $R_4$ represents hydrogen, lower alkyl, carbocyclic or heterocyclic aryl, carbocyclic or heterocyclic aryl-lower alkyl, cycloalkyl, cycloalkyl-lower alkyl, biaryl or biaryl-lower alkyl; $R_6$ and $R_7$ represent $C_1$–$C_4$-alkyl or carbocyclic or heterocyclic aryl-$C_1$–$C_4$-alkyl; $COOR_2$ represents carboxyl or carboxyl derivatized in form of a pharmaceutically acceptable ester; disulfide derivatives derived from said compounds wherein $R_3$ is hydrogen; and pharmaceutically acceptable salts thereof.

Further preferred are said compounds of formula II wherein $R_1$ represents lower alkyl, cycloalkyl, carbocyclic monocyclic aryl, heterocyclic monocyclic aryl, carbocyclic bicyclic aryl, heterocyclic bicyclic aryl or biaryl; $R_3$ represents hydrogen, aryl-lower alkanoyl, lower alkanoyl, or heterocyclic or carbocyclic aroyl; $R_4$ represents hydrogen, lower alkyl or carbocyclic aryl-lower alkyl; $R_6$ and $R_7$ are identical and represent $C_1$–$C_4$ alkyl or carbocyclic aryl-$C_1$–$C_4$-alkyl; $COOR_2$ represents carboxyl, lower alkoxycarbonyl, carbocyclic or heterocyclic aryl-lower alkoxycarbonyl, α-lower alkanoyloxy-, lower alkoxycarbonyl- or di-lower alkylaminocarbonyl-)lower alkoxycarbonyl; and pharmaceutically acceptable salts thereof.

Particularly preferred are said compounds of formula II wherein $R_1$ represents cyclohexyl, phenyl, phenyl substituted by hydroxy, acyloxy, amino, acylamino, lower alkoxy, trifluoromethyl or by halo; or $R_1$ represents biphenylyl, biphenylyl substituted by lower alkyl, lower alkoxy, halogen or by trifluoromethyl, thiazolyl, pyridyl, thienyl, benzothiazolyl, or indolyl; $R_3$ represents hydrogen, lower alkanoyl, benzoyl or pyridylcarbonyl; $R_4$ represents hydrogen, lower alkyl, benzyl or benzyl substituted by hydroxy, halo, lower alkyl, acyloxy, lower alkoxy or trifluoromethyl; $R_6$ and $R_7$ represent methyl or ethyl; $COOR_2$ represents carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; and pharmaceutically acceptable salts thereof.

Further preferred are said compounds of formula II wherein $R_1$ represents phenyl or phenyl substituted by hydroxy, acyloxy derived from a carboxylic acid, halo or lower alkoxy; $R_3$ represents hydrogen or lower alkanoyl; $R_4$ represents lower alkyl, benzyl or benzyl substituted by hydroxy, halo, lower alkyl, lower alkanoyloxy, lower alkoxy or trifluoromethyl; $R_6$ and $R_7$ are identical and represent methyl or ethyl; $COOR_2$ represents carboxyl, lower alkoxycarbonyl, benzyloxycarbonyl, pyridylmethoxycarbonyl, α-(lower alkanoyloxy-, lower alkoxycarbonyl- or di-lower alkylaminocarbonyl-) lower alkoxycarbonyl; and pharmaceutically acceptable salts thereof.

A particular preferred embodiment relates to compounds of any of the above formulas wherein $R_1$ is 4-hydroxyphenyl, 4-acyloxyphenyl, 4-fluorophenyl or 4-methoxyphenyl; $R_3$ is hydrogen or lower alkanoyl; $R_4$ is isopropyl; $R_6$ and $R_7$ are methyl; $COOR_2$ is carboxyl or lower alkoxycarbonyl; and pharmaceutically acceptable salts thereof.

Of particular interest are said compounds wherein $R_1$ represents 4-hydroxyphenyl, 4-methoxyphenyl, 4-(thienylcarbonyloxy)phenyl, 4-(pyridylcarbonyloxy)phenyl, 4-(lower alkoxyacetyloxy)phenyl, 4-lower alkanoyloxyphenyl or 4-(lower alkoxycarbonyloxy)phenyl; $R_3$ represents hydrogen or lower alkanoyl; $R_4$ represents isopropyl; $R_6$ and $R_7$ represent methyl; $COOR_2$ represents carboxyl or lower alkoxycarbonyl; and pharmaceutically acceptable salts thereof.

Particularly preferred are said compounds of formula II wherein $R_1$ represents 4-methoxyphenyl or 4-hydroxyphenyl; $R_3$ represents hydrogen; $R_4$ represents isopropyl; $R_6$ and $R_7$ represent methyl; $COOR_2$ represents carboxyl; ester, S-acyl and O-acyl prodrug derivatives thereof; and pharmaceutically acceptable salts thereof.

The definitions as such or in combination as used herein, unless denoted otherwise, have the following meanings within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substituents, such being advantageously lower alkyl, hydroxy, lower alkoxy, acyloxy, halogen, cyano, trifluoromethyl, amino, lower alkanoylamino, lower alkyl-(thio, sulfinyl or sulfonyl), lower alkoxycarbonyl, mono- or di-lower alkylcarbamoyl, or mono- or di-lower alkylamino.

Bicyclic carbocyclic aryl represents 1- or 2-naphthyl or 1- or 2-naphthyl preferably substituted by lower alkyl, lower alkoxy or halogen.

Monocyclic heterocyclic aryl represents preferably optionally substituted thiazolyl, thienyl, furanyl or pyridyl.

Optionally substituted furanyl represents 2- or 3-furanyl or 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Optionally substituted thiazolyl represents e.g. 4-thiazolyl, or 4-thiazolyl substituted by lower alkyl.

Bicyclic heterocyclic aryl represents preferably indolyl or benzothiazolyl optionally substituted by hydroxy, lower alkyl, lower alkoxy or halogen, advantageously 3-indolyl or 2-benzothiazolyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl; also, optionally substituted naphthyl.

Aryl-lower alkyl is advantageously benzyl or 1- or 2-phenethyl optionally substituted on phenyl by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

Cycloalkyl represents a saturated cyclic hydrocarbon radical which preferably contains 5 to 7 ring carbons, preferably cyclopentyl or cyclohexyl.

The term cycloalkyl(lower)alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Cycloalkylidene is 3 to 10 membered, preferably 5 or 6-membered, and represents a cycloalkane linking group in which the two attached groups are attached to the same carbon of the cycloalkane ring.

Benzo-fused cycloalkylidene represents e.g. 1,1- or 2,2-tetralinylidene or 1,1- or 2,2-indanylidene.

Halogen (halo) preferably represents fluoro or chloro, but may also be bromo or iodo.

Acyl is derived from a carboxylic acid and represents preferably optionally substituted lower alkanoyl, carbocyclic aryl-lower alkanoyl, aroyl, lower alkoxycarbonyl or aryl-lower alkoxycarbonyl, advantageously optionally substituted lower alkanoyl, or aroyl.

Lower alkanoyl is preferably acetyl, propionyl, butyryl, or pivaloyl.

Optionally substituted lower alkanoyl for example represents lower alkanoyl or lower alkanoyl substituted by lower alkoxycarbonyl, lower alkanoyloxy, lower alkanoylthio, lower alkoxy, or by lower alkylthio.

Aroyl is carbocyclic or heterocyclic aroyl, preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Acyloxy is preferably optionally substituted lower alkanoyloxy, lower alkoxycarbonyloxy, monocyclic carbocyclic aroyloxy or monocyclic heterocyclic aroyloxy.

Aryl-lower alkoxycarbonyl is preferably monocyclic carbocyclic-lower alkoxycarbonyl, advantageously benzyloxycarbonyl.

Biaryl represents monocarbocyclic aryl substituted by monocyclic carbocyclic or monocyclic heterocyclic aryl, and preferably represents biphenylyl, advantageous 4-biphenylyl optionally substituted on one or both benzene rings by lower alkyl, lower alkoxy, halogen or trifluoromethyl.

Biaryl-lower alkyl is preferably 4-biphenylyl-lower alkyl, advantageously 4-biphenylyl-methyl.

The novel compounds of the invention are angiotensin converting enzyme (ACE) inhibitors inhibiting the conversion of angiotensin I to the pressor substance angiotensin II and thus decrease blood pressure in mammals. Furthermore, compounds of the invention demonstrate inhibition of neutral endopeptidase (NEP) and thus potentiate the cardiovascular (e.g. diuretic and natriuretic) effects of atrial natriuretic factors (ANF). The combined effect is beneficial for the treatment of cardiovascular disorders in mammals, in particular hypertension and cardiac conditions such as congestive heart failure.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously orally or intravenously, e.g. as a suspension or in aqueous solution. The dosage in vitro may range between about $10^{-6}$ molar and $10^{-9}$ molar concentrations. The dosage in vivo may range depending on the route of administration, between about 0.01 and 50 mg/kg, advantageously between about 0.1 and 25 mg/kg.

In vitro testing is most appropriate for the free carboxylic acids of the invention. The test compound is dissolved in dimethyl sulfoxide, ethanol, or 0.25M sodium bicarbonate solution, and the solution is diluted with buffer to the desired concentration.

The in vitro inhibition of the angiotensin-converting enzyme (ACE) by the compounds of this invention can be demonstrated by a method analogous to that given in Biochem. Pharmacol. 20:1637,1971. The buffer for the ACE assay is 300 mM NaCl, 100 mM $KH_2PO_4$ (pH 8.3). The reaction is initiated by the addition of 100 μl of hippuryl-histidyl-leucine (2 mg/ml) to tubes containing enzyme and drug in a volume of 150 μl and tubes are incubated for 30 minutes at 37° C. The reaction is terminated by the addition of 0.75 ml 0.6N NaOH. 100 μl of freshly prepared 0-pthaldehyde solution (2 mg/ml in methanol) is added to the tubes, the contents are mixed and allowed to stand at room temperature. After 10 minutes, 100 μl of 6N HCl is added. The tubes are centrifuged and the supernatant optical density is read at 360 nm. The results are plotted against drug concentration to determine the $IC_{50}$, i.e., the drug concentration which gives half the activity of the control sample containing no drug.

Illustrative of the invention, the compound of example 2 demonstrates an $IC_{50}$ of about 15 nM in the ACE in vitro assay.

Inhibition of angiotensin convening enzyme can be demonstrated in vivo on oral or intravenous administration by measuring inhibition of the angiotensin I induced pressor response in normotensive rats.

The in vivo test for intravenously administered compounds is performed with male, normotensive rats, which are anesthetized with sodium metofan. A femoral artery and femoral vein are cannulated respectively for direct blood pressure measurement on i.v. administration of angiotensin I and i.v. or p.o. administration of a compound of this invention. After the basal blood pressure is stabilized, pressor responses to 3 challenges of 300 ng/kg angiotensin I i.v., at 15 minute intervals, are obtained. Such pressure responses are usually again obtained at 15, 30, 60 and 90 minutes, and then every hour up to 6 hours after i.v. or p.o. administration of the compound to be tested, and compared with the initial responses. Any observed decrease of said pressor response is an indication of Angiotensin I converting enzyme inhibition.

Illustrative of the invention, the compound of example 2 inhibits the Angiotensin I induced pressor response for 6 hours at a dose of 10 mg/Kg i.v.

The in vitro inhibition of neutral endopeptidase (NEP, EC 3.4.24.11) can be determined as follows:

Neutral endopeptidase 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 μl) contains 4.2 μg of protein (rat kidney cortex membranes prepared by method of Maeda et at, 1983), 50 mM tris buffer, pH 7.4 at 25° C., 500 μM substrate (final concentration), and leucine aminopeptidase M (2.5 μg). The mixture is incubated for 10 minutes at 25° C. and 100 μl of fast garnet (250 μg fast garnet/ml of 10% Tween 20 in 1M sodium acetate, pH 4.2) is added. Enzyme activity is measured spectrophotometrically at 540 nm. One unit of NEP 24.11 activity is defined as 1 nmol of 2-naphthylamine released per minute at 25° C. at pH 7.4. $IC_{50}$ values are determined, i.e. the concentration of test compound required for 50% inhibition of the release of 2-naphthylamine.

Neutral endopeptidase activity can also be determined using ANF as a substrate. Atrial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37° C. for 2 minutes and the reaction is initiated by the addition of 4 nmol of r-ANF in a total volume of 50 μl. The reaction is terminated after 4 minutes with the addition of 30 μl of 0.27% trifluoroacetic acid (TFA). One unit of activity is defined as the hydrolysis of 1 nmol of r-ANF per minute at 37° C. at pH 7.4. $IC_{50}$ values are determined, i.e. the concentration of test compound required for 50% inhibition of the hydrolysis of ANF.

Illustrative of the invention, the compound of example 2 demonstrates an $IC_{50}$ of about 9.2 nM in the GAAP in vitro assay.

The effect of the compounds of the invention on rat plasma ANF concentration can be determined as follows:

Male Sprague-Dawley rats (275–390 g) are anesthetized with ketamine (150 mg/kg)/acepromazine (10%) and instrumented with catheters in the femoral artery and vein to obtain blood samples and infuse ANF, respectively. The rats are tethered with a swivel system and are allowed to recover for 24 hours before being studied in the conscious, unrestrained state.

In the assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180, and 240 minutes after administration of the test compound.

Plasma ANF concentrations are determined by a specific radioimmunoassay. The plasma is diluted (X 12.5, X 25 and X 50) in buffer containing: 50 mM Tris (pH 6.8), 154 mM NaCl, 0.3% bovine serum albumin, 0.01% EDTA. One hundred microliters of standards [rANF (99–126)] or samples are added to 100 µl of rabbit anti-rANF serum and incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supernatant is decanted and the pellets counted in a gamma counter. All determinations are performed in duplicate. Plasma ANF levels are expressed as a percent of those measured in vehicle-treated animals which received ANF alone (450 ng/kg/min i.v.).

The antihypertensive activity can be determined e.g. in the spontaneously hypertensive rat and the DOCA-salt hypertensive rat, e.g. according to Trapani et al, J. Cardiovasc. Pharmacol. 14, 419–424 (1989).

The antihypertensive effect can be determined in desoxycorticosterone acetate (DOCA)-salt hypertensive rats as follows:

DOCA-salt hypertensive rats (280–380 g) are prepared by the standard method. Rats underwent a unilateral nephrectomy and one week later are implanted with silastic pellets containing 100 mg/kg of DOCA. The rats are maintained on 1% NaCl/0.2% KCl drinking water for three to five weeks until sustained hypertension is established. The antihypertensive activity is evaluated at this time.

Two days before an experiment, the rats are anesthetized with methoxyflurane and instrumented with catheters in the femoral artery to measure arterial blood pressure. Forty-eight hours later, baseline arterial pressure and heart rate are recorded during a 1 hour period. The test compound or vehicle is then administered and the same cardiovascular parameters are monitored for an additional 5 hours.

The antihypertensive effect can also be determined in spontaneously hypertensive rats by indirect measurement of systolic pressure. Conscious rats are placed individually in restraint cages within a gently warmed chamber. A rubber pulse sensor is placed distal to an inflatable occlusive cuff on each rat's tail. The cuff is periodically inflated to occlude the tail artery, and systolic pressure is recorded as the point where the first discernible pulse emerges along the decaying calibrated pressure curve. After obtaining control values of blood pressure and heart rate, test compounds are administered orally once daily for 4 consecutive days. Additional blood pressure measurements are usually made at 2.0, 4.0 and 23.5 hours after each daily dosing, and responses are compared to those of rats dosed with the treatment vehicle.

The diuretic (saluretic) activity can be determined in standard diuretic screens, e.g. as described in "New Antihypertensive Drugs", Spectrum Publications, 1976, pages 307–321, or by measuring the potentiation of atrial natriuretic factor-induced natriuresis and diuresis in the rat.

The potentiation of the natriuretic effect of ANF can be determined as follows:

Male Sprague-Dawley rats (280–360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 µl/min) is maintained throughout the experiment to promote diuresis and sodium excretion. The experimental protocol consists of an initial 15 minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control; 15 minutes). At the conclusion of this period, ANF is administered (1 µg/kg i.v. bolus) to all animals and arterial pressure and renal parameters are determined during two consecutive 15 minutes collection periods. Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

The compounds of the invention, e.g. can be prepared (a) by condensing a compound of formula III

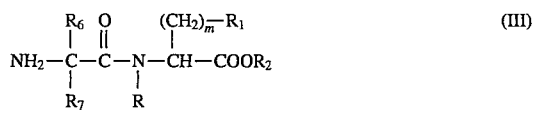

wherein the symbols m, R, $R_1$, $R_6$ and $R_7$ have the meaning as defined above and $COOR_2$ represents esterified carboxyl, with a carboxylic acid of the formula IV

or a reactive functional derivative thereof, wherein $R_4$ and $R_5$ have meaning as defined above, $R_3'$ represents hydrogen or a labile S-protecting group, e.g. acyl, t-butyl or optionally substituted benzyl; or (b) by condensing a compound of the formula V

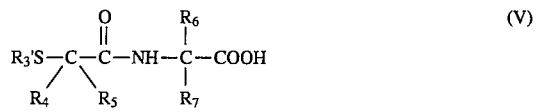

or a reactive functional derivative thereof wherein the symbols $R_3'$ and $R_4$–$R_5$ have meaning as defined above, with an amino acid ester of the formula VI

wherein m, R and $R_1$ have meaning as defined above and $COOR_2$ represents esterified carboxyl; or c) by condensing under basic conditions a compound of the formula VII

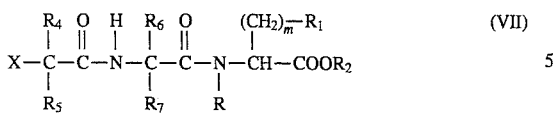  (VII)

wherein the symbols R, $R_1$, $R_2$ and $R_4$–$R_7$ and m have meaning as defined above and X represents a reactive esterified hydroxyl group (e.g. chloro or bromo) as a leaving group, with a compound of the formula

  (VIII)

wherein $R_3'$ represents a labile S-protecting group, e.g. acyl, t-butyl or optionally substituted benzyl; and converting a resulting product wherein $R_3'$ is optionally substituted benzyl to a compound of formula I wherein $R_3$ is hydrogen; and in above said process, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

In starting compounds and intermediates which are convened to the compounds of the invention in manner described herein, functional group present, such as thiol, carboxyl, amino and hydroxy groups, are optionally protected by conventional protecting groups that are common in preparative organic chemistry. Protected thiol, carboxyl, amino and hydroxy groups are those that can be convened under mild conditions into free thiol, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (thiol, carboxyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, N.Y. 1973, T. W. Greene and P.G.M. Woots, "Protective Groups in Organic Synthesis", Wiley, N.Y. 1991, and also in "The Peptides", Vol. I, Schroeder and Luebke, Academic Press, London, N.Y., 1965.

The preparation of compounds of the invention according to process (a) involving the condensation of an amine of formula HI with the acid of formula IV or a functional reactive derivative thereof, is carried out by methodology well-known for peptide synthesis.

The condensation according to process (a) of an amino ester of formula III with a free carboxylic acid of formula IV is carried out advantageously in the presence of a condensing agent such as dicyclohexylcarbodiimide or N-(3-dimethylaminopropyl)-N'-ethylcarbodiimide and hydroxybenzotriazole, 1-hydroxy-7-azabenzotriazole, chloro dimethoxy triazine or benzotriazol-1-yloxytris(dimethylamino)phosphonium hexafluorophosphate (BOP Reagent), and triethylamine or N-methylmorpholine, in an inert polar solvent such as dimethylformamide of methylene chloride, preferably at room temperature.

The condensation of an amino ester of formula III with a reactive functional derivative of an acid of formula IV in the form of an acid halide, advantageously an acid chloride, or mixed anhydride, is carried out in an inert solvent such as toluene or methylene chloride, advantageously in the presence of a base, e.g. an inorganic base such as potassium carbonate or an organic base such as triethylamine, N-methylmorpholine or pyridine, preferably at room temperature.

Reactive functional derivatives of carboxylic acids of formula IV are preferably acid halides (e.g. the acid chloride) and mixed anhydrides, such as the pivaloyl or isobutyloxycarbonyl anhydride, or activated esters such as benzotriazole, 7-azabenzotriazole or hexafluorophenyl ester.

The starting material of formula III can be prepared according to methods described herein and illustrated in the examples.

The preparation of a starting material of formula III involves the acylation of an ester of the amino acid of formula IX

  (IX)

wherein m, R and $R_1$ have meaning as defined hereinabove and $COOR_2$ represents esterified carboxyl (e.g. wherein $R_2$ is lower alkyl or benzyl) with an appropriately N-protected gem-disubstituted amino acid (or a reactive functional derivative) of formula X

  (X)

wherein A has meaning as defined hereinabove and $R_8$ is a labile amino protecting group, e.g. t-butoxycarbonyl, to obtain the corresponding N-protected compound of formula III.

The condensation of a compound of formula IX with a compound of formula X is carried out by methodology well known in peptide synthesis, e.g. as described above for the condensation of a compound of formula III with a compound of formula IV. The N-protecting group is removed according to methods well-known in the art, e.g. the t-butoxycarbonyl is removed with anhydrous acid such as trifluoroacetic acid.

The starting amino acids and esters of compounds of formula IX and X are either known in the art or if new can be prepared according to methods well-known in the art, e.g. from the corresponding aldehyde or ketone. The amino acids of formula IX are preferably obtained as the -S- enantiomers.

The starting materials of formula IV are known or if new may be prepared according to conventional methods. The starting materials are prepared e.g. from the corresponding racemic or optically active α-amino acids, by conversion thereof to the α-bromo derivative followed by displacement thereof with the appropriate thio acids or optionally substituted benzylthiol, under basic conditions, for example as illustrated in European Patent application No. 524,553 published Jan. 27, 1993. S-Debenzylation of the resulting final products is carried out by reductive cleavage, e.g. with Raney nickel in ethanol. S-deacylation is carried out by e.g. base catalyzed hydrolysis with dilute aqueous sodium hydroxide. Cyclic starting materials of formula IV can be prepared by treatment of the cyclic carboxylic acid (e.g. cyclopentanecarboxylic acid) with sulfur in the presence of a strong base such as lithium diethylamide.

The preparation of the compounds of the invention according to process (b) involving the condensation of an acid of formula V with an amino acid ester of formula VI is carried out in a similar fashion to process (a). Similarly the starting materials of formula V are prepared by condensation of an acid of formula IV with an ester corresponding to gem-disubstituted amino acids of formula X (wherein $R_8$ is now hydrogen) under conditions similar to those described above, followed by removal of the carboxyl protecting group.

The preparation of the compounds of the invention according to process (c) involving the displacement of a leaving group X in a compound of formula VII with a sulfhydryl derivative $R_3'$-SH is carried out according to methods well-known in the art.

A reactive esterified hydroxyl group, represented by X, is a hydroxyl group esterified by a strong inorganic or organic acid. Corresponding X groups are in particular halo, for example chloro, bromo or iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The displacement is carried out in an inert solvent, such as dimethylformamide or methylene chloride in the presence of a base such as potassium carbonate, triethylamine, diisopropylethylamine, N-methylmorpholine, and the like at room or elevated temperature.

Similarly, the starting materials of formula VII can be prepared by reacting the dipeptide derivative of formula III with an acid of the formula

wherein $R_4$ and $R_5$ and X have meaning as defined above, under conditions described for process (a).

Certain compounds of the invention and intermediates can be converted to each other according to general reactions well known in the art.

The free mercaptans may be converted to the S-acyl derivatives by reaction with a reactive derivative of a carboxylic acid (corresponding to $R_3$ being acyl in formula I), such as an acid anhydride or said chloride, preferably in the presence of cobalt chloride ($CoCl_2$) in an inert solvent such as acetonitrile or methylene chloride.

Free alcohols and phenols can be converted to the corresponding acyl derivatives e.g. by reaction with a corresponding acid chloride in the presence of a base, such as triethylamine.

The free mercaptans, wherein $R_3$ represents hydrogen, may be oxidized to the corresponding disulfides, e.g. by air oxidation or with the use of mild oxidizing agents such as iodine in alcoholic solution. Conversely, disulfides may be reduced to the corresponding mercaptans, e.g. with reducing agents such as sodium borohydride, zinc and acetic acid or tributylphosphine.

Carboxylic acid esters may be prepared from a carboxylic acid by condensation with e.g. the halide corresponding to $R_2$-OH, in the presence of a base, or with an excess of the alcohol in the presence of an acid catalyst, according to methods well-known in the art.

Carboxylic acid esters and S-acyl derivatives may be hydrolyzed, e.g. with aqueous alkali such as alkali metal carbonates or hydroxides.

In case mixtures of stereoisomers (e.g. diastereomers) are obtained, these can be separated by known procedures such as fractional crystallization and chromatography (e.g. thin layer, column, flash chromatography). Racemic free acids can be resolved into the optical antipodes by fractional crystallization of d- or l-(α-methylbenzylamine, cinchonidine, cinchonine, quinine, quinidine, dehydroabietylamine, brucine or strychnine) salts and the like. Racemic products, if not diastereoisomers, can first be converted to diastereoisomers with optically active reagents (such as optically active alcohols to form esters) which can then be separated as described above, and e.g. hydrolyzed to the individual enantiomer. Racemic products can also be resolved by chiral chromatography, e.g. high pressure liquid chromatography using a chiral adsorbent; also by enzymatic resolution, e.g. of esters with alkalase.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, for inhibiting angiotensin convening enzyme (ACE) and neutral endopeptidase (NEP), and e.g. for the treatment of cardiovascular disorders such as hypertension, edema, salt retention and congestive heart failure.

The present invention also relates to the use of the compounds of the invention for the preparation of pharmaceutical compositions especially pharmaceutical compositions having angiotensin convening enzyme and neutral endopeptidase inhibiting activity, and e.g. antihypertensive activity.

The pharmaceutical compositions according to the invention are those suitable for enteral, such as oral or rectal, transdermal and parenteral administration to mammals, including man, for the treatment of cardiovascular disorders, such as hypertension, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and, if desired, absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 5 and 50 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium) or other wavelengths as specified in the examples.

The prefixes R and S are used to indicate the absolute configuration at each asymmetric center.

EXAMPLE 1

To a stirred solution of N-(2-amino-2-methyl-1-oxopropyl)-L-tyrosine ethyl ester monohydrochloride (1.33 g, 3.70 mmol) in dimethylformamide (50 mL) and triethylamine (0.52 mL, 3.70 mmol) is added (S)-2-acetylthio-3-methylbutanoic acid (0.65 g, 3.70 mmol). To this mixture is added 1-hydroxy-7-azabenzotriazole (0.55 g, 4.07 mmol) and 1,3-dicyclohexylcarbodiimide (0.84 g, 4.07 mmol). The mixture is stirred overnight and then water (50 mL) is added to the mixture. The solution is extracted with ethyl acetate (3×50 mL). The combined organic layers are washed with a saturated solution of sodium bicarbonate (20 mL), brine, dried over magnesium sulfate and the solvent is removed to give a yellow foam. The foam is purified by flash chromatography ($SiO_2$:hexane/ethyl acetate, 6:4) to give as a white solid N-[2-(2(S)-acetylthio-3-methyl-1-oxobutylamino)-2-methyl-1-oxopropyl]-L-tyrosine ethyl ester, m.p. 137°–138° C., the compound of formula II wherein $R_1$ is 4-hydroxyphenyl, $R_2$ is ethyl, $R_3$ is acetyl, $R_4$ is isopropyl, and $R_6$ and $R_7$ are methyl.

The starting material is prepared as follows:

To a stirred solution of L-tyrosine ethyl ester (2.10 g, 10.0 mmol) and N-t-butoxy-carbonyl-α-methylalanine (2.03 g, 10.0 mmol) in dimethylformamide (40 mL) is added 1,3-dicyclohexylcarbodiimide (2.26 g, 11.0 mmol) and 1-hydroxybenzotriazole (1.48 g, 11.0 mmol). The mixture is stirred overnight and then water (50 mL) is added. The aqueous phase is extracted with ethyl acetate (3×75 mL). The combined organic phases are washed with a saturated solution of sodium bicarbonate (25 mL), brine, dried over magnesium sulfate and the solvent is removed to give a light yellow oil. The oil is purified by flash chromatography ($SiO_2$:hexane/ethyl acetate) to afford N-[2-(t-butoxy-carbonylamino)-2-methyl-1-oxopropyl]-L-tyrosine ethyl ester as a white solid.

Into a stirred solution of N-[2-(t-butoxycarbonylamino)-2-methyl-1-oxopropyl]-L-tyrosine ethyl ester (1.46 g, 3.70 mmol) in ethyl acetate (50 mL) and methanol (10 mL) is bubbled hydrochloric acid gas for 10 minutes. The solvent is removed to give N-(2-amino-2-methyl-1-oxopropyl)-L-tyrosine ethyl ester monohydrochloride as a white foam which is used without any further purification.

EXAMPLE 2

To a solution of N-[2-(2(S)-acetylthio-3-methyl-1-oxobutylamino)-2-methyl-1-oxopropyl]-L-tyrosine ethyl ester (0.18 g, 0.39 mmol) in methanol (10 mL) is added 1N sodium hydroxide (1.55 mL, 1.55 mmol). The mixture is stirred for 5 hours and then the solvent is removed in vacuo. The residue is dissolved in water (50 mL) and washed with ethyl acetate (10 mL). The aqueous phase is acidified to pH 1 with 1N hydrochloric acid and extracted with ethyl acetate (3×50 mL). The organic phase is washed with brine, dried over magnesium sulfate and the solvent is concentrated to yield a clear oil which is crystallized from ethyl ether to give N-[2-(2(S)-mercapto-3-methyl-1-oxobutylamino)-2-methyl-1-oxopropyl]-L-tyrosine, m.p. 180°–181° C., the compound of formula II wherein $R_1$ is 4-hydroxyphenyl, $R_2$ and $R_3$ are hydrogen, $R_4$ is isopropyl, and $R_6$ and $R_7$ are methyl.

EXAMPLE 3

Prepared similarly to the previous examples are the following:

(a) the compound of formula II wherein $R_1$ is 4-methoxyphenyl, $R_2$ is ethyl, $R_3$ is acetyl, $R_4$ is isopropyl, and $R_6$ and $R_7$ are methyl;

(b) the compound of formula II wherein $R_1$ is 4-methoxyphenyl, $R_2$ and $R_3$ are hydrogen, $R_4$ is isopropyl and $R_6$ and $R_7$ are methyl;

(c) the compound of formula II wherein $R_1$ is 4-hydroxyphenyl, $R_2$ and $R_3$ are hydrogen, $R_4$ is benzyl and $R_6$ and $R_7$ are methyl;

(d) the compound of formula II wherein $R_1$ is 4-hydroxyphenyl, $R_2$ and $R_3$ are hydrogen, $R_4$ is isopropyl, and $R_6$ and $R_7$ are phenylethyl;

(e) the compound of formula II wherein $R_1$ is 4-methoxyphenyl, $R_2$ and $R_3$ are hydrogen, $R_4$ is isopropyl, $R_6$ is benzyl and $R_7$ is methyl;

(f) the compound of formula II wherein $R_1$ is 2-thienyl; $R_2$ and $R_3$ are hydrogen, $R_4$ is isopropyl, and $R_6$ and $R_7$ are methyl;

(g) the compound of formula II wherein $R_1$ is 3-indolyl; $R_2$ and $R_3$ are hydrogen; $R_4$ is isopropyl, and $R_6$ and $R_7$ are methyl;

(h) the compound of formula II wherein $R_1$ is 4-methoxyphenyl, $R_2$ is acetyl, $R_3$ is ethyl, $R_4$ is benzyl, and $R_6$ and $R_7$ are methyl.

EXAMPLE 4

(a) To a solution of N-[2-(2(S)-acetylthio-3-methyl-1-oxobutylamino)-2-methyl-1-oxopropyl]-L-tyrosine ethyl ester (0.10 g, 0.23 mmol) in 5 mL methylene chloride is added triethylamine (0.032 mL, 0.23 mmol) followed by 2-thiophenecarbonyl chloride (0.034 g, 0.23 mmol). The reaction mixture is stirred at room temperature for 1 hour. Water is added, the methylene chloride layer is separated, washed with water, dried over $MgSO_4$ and evaporated to dryness. The resulting solid is recrystallized from ether to yield the compound of formula II wherein $R_1$ is 4-(2-thienylcarbonyloxy)-phenyl, $R_2$ is ethyl, $R_3$ is acetyl, $R_4$ is isopropyl, and $R_6$ and $R_7$ are methyl.

EXAMPLE 5

To a stirred solution of 1-mercapto-1-cyclopentylcarboxylic acid (1.74 g) in dichloromethane (50 mL) and triethylamine (0.63 mL) is added N-(2-amino-2-methyl-1-oxopropyl)-L-tyrosine ethyl ester monohydrochloride (0.80 g).

To this solution is added 1-hydroxy-7-azabenzotriazole (0.68 g) 1,3-dicyclohexylcarbodiimide (1.03 g). The mixture is stirred overnight and then the solid precipitate is removed by filtration. The organic phase is washed with a saturated solution of sodium bicarbonate (10 mL), brine (10 mL), dried over magnesium sulfate and the solvent is removed to give a clear oil. The oil is purified by flash chromatography ($SiO_2$, hexane/ethyl acetate 6:4) to give N-[2-[(1-mercapto-1-cyclopentylcarbonyl)-amino]-2-methyl-1-oxopropyl]-L-tyrosine ethyl ester, the compound of formula I wherein $R_1$ is 4-hydroxyphenyl, $R_2$ is ethyl, R and $R_3$ are hydrogen, $R_4$ and $R_5$ together with the carbon to which they are attached represent cyclopentylidene, $R_6$ and $R_7$ are methyl, and m is 1.

EXAMPLE 6

Preparation of 3000 capsules each containing 20 mg of the active ingredient, for example the compound of formula II wherein $R_1$ is 4-hydroxyphenyl, $R_2$ is ethyl, $R_3$ is acetyl, $R_4$ is isopropyl, and $R_6$ and $R_7$ are methyl.

| Active ingredient | 60.00 g |
|---|---|
| Lactose | 750.00 g |
| Microcrystalline cellulose | 300.00 g |
| Polyvinylpyrrolidone | 30.00 g |
| Purified water | q.s. |
| Magnesium stearate | 9.0 g |

The active ingredient is passed through a No. 30 hand screen.

The active ingredient, lactose, cellulose and polyvinylpyrrolidone are blended for 15 minutes in a mixer. The blend is granulated with sufficient water (about 500 mL), dried in an oven at 35° C. overnight, and passed through a No. 20 screen.

Magnesium stearate is passed through a No. 20 screen, added to the granulation mixture, and the mixture is blended for 5 minutes in a mixer. The blend is encapsulated in No. 0 hard gelatin capsules each containing an mount of the blend equivalent to 20 mg of the active ingredient.

What is claimed is:

1. A compound of the formula I

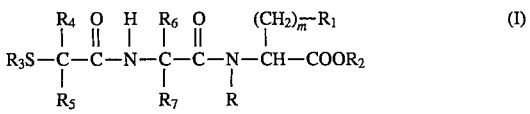

wherein

R represents hydrogen, lower alkyl, carbocyclic or heterocyclic aryl-lower alkyl or cycloalkyl-lower alkyl;

$R_1$ represents hydrogen, lower alkyl, cycloalkyl, carbocyclic aryl or heterocyclic aryl, or biaryl;

$R_3$ represents hydrogen or acyl;

$R_4$ represents hydrogen, lower alkyl, carbocyclic or heterocyclic aryl, carbocyclic or heterocyclic aryl-lower alkyl, cycloalkyl, cycloalkyl-lower alkyl, biaryl or biaryl-lower alkyl;

$R_5$ represents hydrogen or lower alkyl; or $R_4$ and $R_5$ together with the carbon atom to which they are attached represent cycloalkylidene or benzo-fused cycloalkylidene;

$R_6$ represents carbocyclic or heterocyclic aryl, carbocyclic or heterocyclic aryl-lower alkyl, cycloalkyl, cycloalkyl-lower alkyl, biaryl or biaryl-lower alkyl;

$R_7$ represents carbocyclic or heterocyclic aryl-lower alkyl, cycloalkyl-lower alkyl or biaryl-lower alkyl;

m is 0, 1, 2 or 3; and $COOR_2$ represents carboxyl or carboxyl derivatized in form of a pharmaceutically acceptable ester;

a disulfide derivative derived from said compound wherein $R_3$ is hydrogen; or a pharmaceutically acceptable salt thereof.

2. A compound according to claim 1 having the configuration of formula Ia

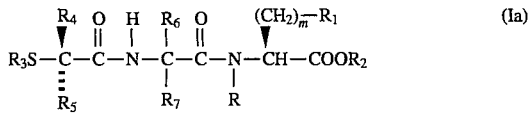

wherein m, R and $R_1$–$R_7$ have meaning as defined in said claim.

3. A compound according to claim 1 of the formula II

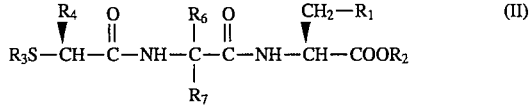

wherein $R_1$ represents lower alkyl, $C_5$- or $C_6$-cycloalkyl, carbocyclic or heterocyclic monocyclic or bicyclic aryl, or biaryl; $R_3$ represents hydrogen or acyl; $R_4$ represents hydrogen, lower alkyl, carbocyclic or heterocyclic aryl, carbocyclic or heterocyclic aryl-lower alkyl, cyclo, alkyl, cycloalkyl-lower alkyl, biaryl or biaryl-lower alkyl; $R_6$ and $R_7$ represent carbocyclic or heterocyclic aryl-$C_1$–$C_4$-alkyl; $COOR_2$ represents carboxyl or carboxyl derivatized in form of a pharmaceutically acceptable ester; a disulfide derivative derived from said compound wherein $R_3$ is hydrogen; or a pharmaceutically acceptable salt thereof.

4. A compound according to claim 3 of formula II wherein $R_1$ represents lower alkyl, cycloalkyl, carbocyclic monocyclic aryl, heterocyclic monocyclic aryl, carbocyclic bicyclic aryl, heterocyclic bicyclic aryl or biaryl; $R_3$ represents hydrogen, aryl-lower alkanoyl, lower alkanoyl; or heterocyclic or carbocyclic aroyl; $R_4$ represents hydrogen, lower alkyl or carbocyclic aryl-lower alkyl; $R_6$ and $R_7$ are identical and represent carbocyclic aryl-$C_1$–$C_4$-alkyl; $COOR_2$ represents carboxyl, lower alkoxycarbonyl, carbocyclic or heterocyclic aryl-lower alkoxycarbonyl, α-(lower alkanoyloxy-, lower alkoxycarbonyl- or di-lower alkylaminocarbonyl-)lower alkoxycarbonyl; n is 2, 4 or 5; or a pharmaceutically acceptable salt thereof.

5. A method for the treatment of cardiovascular disorders comprising administering to a mammal in need thereof an effective amount of a compound of claim 1 or of a compound of claim 1 in combination with one or more pharmaceutically acceptable carriers.

6. A method according to claim 5 for the treatment of hypertension, edema, salt retention or congestive heart failure.

* * * * *